United States Patent [19]

Nicolau et al.

[11] Patent Number: 5,854,171
[45] Date of Patent: Dec. 29, 1998

[54] HONEYCOMB CATALYST FOR VINYL ACETATE SYNTHESIS

[75] Inventors: Ioan Nicolau; Philip M. Colling; Leland R. Johnson, all of Corpus Christi, Tex.

[73] Assignee: Celanese International Corporation, Dallas, Tex.

[21] Appl. No.: 933,649

[22] Filed: Sep. 19, 1997

Related U.S. Application Data

[62] Division of Ser. No. 627,960, Apr. 2, 1996, Pat. No. 5,705, 679.

[51] Int. Cl.[6] .................................................... B01J 37/03
[52] U.S. Cl. ......................... 502/330; 502/300; 502/159; 502/439; 560/245
[58] Field of Search ................................. 502/330, 300, 502/302, 439, 243, 65, 159; 560/245

[56] References Cited

U.S. PATENT DOCUMENTS

| 4,483,940 | 11/1984 | Ono et al. | 502/159 |
| 5,371,277 | 12/1994 | Matsumoto et al. | 560/245 |

FOREIGN PATENT DOCUMENTS 1521652  8/1978  Germany .

*Primary Examiner*—Gary Geist
*Assistant Examiner*—Sreeni Padmanabhan
*Attorney, Agent, or Firm*—M. Susan Spiering; Donald R. Cassady

[57] ABSTRACT

A catalyst particularly useful in the preparation of unsaturated esters such as the reaction of ethylene, oxygen and acetic acid in a vapor phase to form vinyl acetate. The catalyst comprises a honeycomb carrier coated with silica and containing palladium and gold throughout the silica coat. Such catalysts show reduced pressure drop and a high space time yield for vinyl acetate.

20 Claims, No Drawings

HONEYCOMB CATALYST FOR VINYL ACETATE SYNTHESIS

This application is a division of application Ser. No. 08/627,960 filed Apr. 2, 1996 which application is now: U.S. Pat. No. 5,705,679.

BACKGROUND OF THE INVENTION

The present invention relates to a novel catalyst for producing unsaturated esters by gas phase reaction. In particular, this invention is directed to a novel catalyst and a method of using same in the gas phase reaction of ethylene, oxygen and acetic acid to form vinyl acetate.

It is known to produce vinyl acetate by reacting ethylene, oxygen and acetic acid in a gaseous phase and in the presence of a catalyst comprising palladium, gold and an alkali metal acetate supported on certain carrier materials such as silica. Such catalytic systems can exhibit high activity. Results utilizing such palladium and gold catalysts have been somewhat inconsistent. This inconsistency appears to be based somewhat on the distribution pattern or profile of the catalyst components which are deposited on and in relation to the carrier. For example, when use is made of known vinyl acetate catalyst systems comprising a porous support with palladium and gold, the metal components deposited at or about the carrier interiors or central regions do not always contribute significantly to reaction mechanisms, since reactants are not readily able to diffuse into the central or inner regions of the porous network of the catalyst. More importantly, products of catalyst synthesis formed in the catalyst interior must diffuse from the interior outward, again coming into contact with the active phase in the outer region of the catalyst. Consequently, these interior-formed products undergo further reaction and are often converted to unuseful by-products. The most effective reactions occur when the catalytic metal is formed as a thin shell on the surface regions of the catalyst as diffusion of reactants and products can be readily achieved to provide good product yields and reduced by-product formulation.

Various patents have been granted based on the desire to more evenly distribute and anchor gold and palladium catalytic components within a narrow band on a carrier surface to provide a vinyl acetate catalyst having high yield, good selectivity and long life. Examples of such patents include U.S. Pat. Nos. 4,087,622; 4,048,096; 3,822,308; 3,775,342 and British Patent 1,521,652.

The basic method of forming a vinyl acetate catalyst containing palladium and gold deposited on a catalyst carrier comprises (1) impregnating the carrier with aqueous solutions of water-soluble palladium and gold compounds, (2) precipitating water-insoluble palladium and gold compounds on the catalyst carrier by contacting the impregnated catalyst carrier with a solution of compounds capable of reacting with the water-soluble palladium and gold compounds to form the water-insoluble precious metal compounds, (3) washing the treated catalyst with water to remove anions which are freed from the initially impregnated palladium and gold compounds during precipitation, and (4) converting the water-insoluble palladium and gold compounds to free metal by treatment with a reducing agent. A final treatment can involve (5) impregnating the reduced catalyst with an aqueous alkali metal acetate solution and (6) drying the final catalyst product.

Attempts to provide a uniform distribution of the palladium and gold metals on a carrier have involved manipulation of the above mentioned steps. Particularly useful improvements in preparing highly active catalysts for preparing vinyl acetate are described in commonly assigned U.S. Pat. Nos. 5,314,858 and 5,332,710 both of which are herein incorporated by reference. These two patents describe processes for improving palladium and gold distribution on a carrier by manipulating precipitation step (2), the "fixing" of the water soluble precious metal compounds to the carrier as water insoluble compounds. In U.S. Pat. No. 5,314,858, fixing precious metals on the carrier is achieved utilizing two separate precipitation stages to avoid using large excesses of "fixing" compound. U.S. Pat. No. 5,332,710 describes fixing the precious metals by rotating impregnated catalyst carriers while the impregnated carriers are immersed in a reaction solution at least during the initial precipitation period. Such a roto-immersion procedure has been found to yield catalysts in which the precipitated carrier metals are more evenly distributed in a narrow band on the carrier surface.

Other attempts to improve catalytic activity have involved using catalyst carriers of particular pore size or particular shapes. Catalyst carriers useful for producing vinyl esters are typically composed of silica, alumina, aluminum silicates or spinels. Silica is the preferred carrier material because silica is porous and is a neutral carrier for precious metal deposition. The carriers are usually shaped as spheres, tablets or cylinders. Spherical shaped carriers having diameters in the range of 4–8 mm often are employed.

It is preferable, for the purpose of producing an unsaturated ester on an industrial scale, to increase the raw material gas volume comprised of olefin, organic carboxylic acid and oxygen passing across the catalyst as the catalytic activity increases. Catalytic activity is usually evaluated by space time yield (STY). One reason to increase raw material gas volume passing across a catalyst is to prevent formation of hot spots on the catalyst. Since formation reactions of unsaturated esters are exothermic, an increase in catalytic activity can excessively heat portions of the catalyst. Inefficient heat distribution on a catalyst undesirably leads to side reactions such as formation of carbon dioxide which results in less selectivity for formation of the unsaturated ester such as vinyl acetate.

Unfortunately, an increase in raw material gas volume naturally creates a problem of increasing pressure drop in the catalyst layer. This phenomenon of increasing pressure drop has been a barrier against advantageous commercial production of unsaturated esters, in particular when it is attempted to employ a highly active catalyst using existing equipment. While catalytic activity has been improved by modification of catalyst formation or modification of carrier shape or the like, there still remains a large obstacle to achieving an economically advantageous method of producing unsaturated esters, including the obstacle of pressure drop when increasing the volume of raw material gas volume to make efficient use of present increased catalyst activity.

EP 0464633 A1 assigned to Kuraray Co., Ltd. discloses a catalyst developed for the purpose of minimizing pressure drop caused by an increase in raw material gas during unsaturated ester synthesis. EP 0464633 A1 discloses catalyst carriers for vinyl acetate production comprising at least one tubular channel and suggests that such carriers can comprise a hollow cylinder, a ring, a honeycomb or a block having cross channels. Such carriers are disclosed as composed of silica and/or alumina. The active catalytic agents on such carriers include elements selected from Group VIII of the Periodic Table such as palladium and also a promoter selected from Group 1b such as gold. Preferably, a second promoter which is an alkali metal compound of an element selected from Group 1a also is employed. EP 0464633 A1 alleges that the hollow catalytic carriers have the advantage of good heat distribution and low pressure drop, thus providing a higher reaction rate and reducing the number of undesirable side reactions, and increasing the selectivity of reactions for desired end products.

Although honeycomb carriers are listed among the hollow tube carriers suggested in EP 0464633 A1, honeycombs as far as the inventors are aware have never been commercially prepared from alumina or silica. It is believed all commercial honeycombs such as for catalyst use comprise ceramics such as cordierite, a magnesium aluminosilicate; mullite, an aluminosilicate; or cordierite-mullite, a magnesium aluminosilicate-aluminosilicate combination. Such material is too dense and non-porous to serve as the carrier for the palladium and gold metals used in the catalytic preparation of vinyl esters. The catalytic metals would not be sufficiently anchored to the ceramic carrier to provide an effective amount of active catalyst sites. It is further believed that even if honeycombs could be composed of silica or alumina, such carriers would not be practical in processes for preparing unsaturated esters, especially in commercial operations. Under process conditions for preparing unsaturated esters such carriers of silica or alumina may crack or become too brittle to continue to support selective catalytic unsaturated ester synthesis. Cracking or brittleness may also lead to uneven heat distribution and increased pressure drop.

Although hollow catalysts are known, including a suggestion of honeycombs having one or at least 2 pass-through channels for the synthesis of unsaturated esters such as vinyl acetate, there still is a need for an improved honeycomb catalyst containing catalytic agents such as palladium and gold having improved durability, a high activity, and an improved selectivity for unsaturated esters.

Accordingly, it is an object of the present invention to provide for an improved honeycomb catalyst for selective synthesis of vinyl acetate.

Another object of the present invention is to provide for a honeycomb catalyst having improved durability in commercial unsaturated ester synthesis.

Other objects and advantages of the present invention are set forth in the description which follows and will become apparent upon practicing the present invention.

SUMMARY OF THE INVENTION

It now has been found that a catalyst comprising a honeycomb carrier having a silica coat applied thereon and wherein the silica coat supports palladium and gold is particularly useful for the synthesis of unsaturated esters such as vinyl esters from ethylene, lower carboxylic acids with 2–4 carbon atoms and oxygen in a gas phase at elevated temperature and at normal or elevated pressure. The use of the honeycomb catalysts of this invention results in more activity as well as lower pressure drop across the catalyst. Better vapor flow to provide improved heat distribution and to prevent undesirable side reactions is achieved relative to previously suggested catalysts.

The silica coated honeycomb carriers of the present invention eliminate problems of cracking and brittleness which could occur in hypothetical honeycomb carriers composed merely of silica or alumina, especially under commercial conditions used to prepare the vinyl ester. Moreover, since the commercial ceramic honeycombs, such as cordierite, are not porous enough to effectively hold catalytic metals such as palladium and gold for vinyl acetate synthesis, the honeycomb carriers of this invention coated with porous, neutral silica provide a suitable bed to anchor the catalytic agents, and also have an increased surface area within the honeycomb cells for more uniform absorption of the catalytic agents. What has been found is that high catalytic activity with respect to the formation of vinyl esters, such as vinyl acetate, by the process of reacting ethylene, a lower carboxylic acid and oxygen in a gas phase can be maintained and that vinyl ester selectivity can be improved with a honeycomb catalyst of this invention as more fully described below.

DETAILED DESCRIPTION OF THE INVENTION

The improved catalysts of the present invention comprise a honeycomb carrier coated with at least one layer of silica and catalytic agents of palladium and gold supported on the silica layer coating. The carrier material for catalysts of the present invention has a honeycomb structure. For example, such a carrier can be shaped as drums, blocks or cylinders having tubular shaped cells, square or hexagonal shaped cells, as a honeycomb, extending the entire length of the carrier. Cell density per carrier can range from 100 cells/in$^2$ to 400 cells/in$^2$, preferably from 200 cells/in$^2$ to 400 cells/in$^2$. The size of the honeycomb carrier can vary and will depend upon the size of the reactor employed to synthesize an unsaturated ester.

The honeycomb carrier material can be made from any strong material such as metals or ceramic material. Such metals include, but are not limited to, aluminum, titanium, cobalt, steel and the like. Ceramic materials include, but are not limited to, aluminosilicate such as mullite, magnesium aluminosilicate such as cordierite, a combination of magnesium aliminosilicate-aluminosilicate such as cordierite-mullite and the like. Such ceramic carriers are described in U.S. Pat. Nos. 3,894,965; 3,873,469; 3,856,707; and 4,056,489 the entire disclosures which are hereby incorporated herein in their entirety by reference. The most useful materials to provide the honeycomb are non-porous or low porous materials which can withstand the process conditions used in the synthesis of unsaturated esters under commercial operations. The catalyst honeycomb carriers of the present invention will typically have a pore volume as measured by mercury porosimetry of less than about 0.4 cc/g. While porosities greater than 0.4 cc/g are useful, such porous carriers may not need, but preferably have, the silica coat. Carriers can be formed by any suitable process including, for example, molding, pressing, extruding or die stamping, etc.

Because the most desired carrier materials are relatively non-porous, the catalytic carrier, including cell surfaces of the honeycomb catalyst carrier, are coated with at least one layer of silica to provide a porous bed to receive the catalytic agents of palladium and gold. The silica layer increases the surface area of each cell of the honeycomb carrier such that when a catalytic agent is applied to each cell the catalytic material is uniformly distributed over the surface of each cell resulting in improved selectivity for a desired reaction end product during unsaturated ester synthesis. Additionally, a lowered pressure drop in the honeycomb carrier cells reduces resistance to vapor flow during the vapor phase reaction allowing better vapor penetration of cells and contact with the catalytic agents in the interior of the cells, thus increasing the yield for a desired end product.

Specific surface area of the silica coat can vary from about 50–500 m$^2$/g (measured according to BET) and is formed of micropores having a pore volume as measured by mercury porosimetry of about 0.3 to about 1.0 cc/g, or which at least 60% have a diameter of from about 40 to about 400 angstroms.

Silica which coats the surface of each cell can be applied to the honeycomb carrier by any suitable method in the art. One method for coating silica on a carrier is by wet coating. An aqueous slurry of silica is prepared and the slurry is coated on the honeycomb carrier as a layer or multiple layers according to the art. The methods used to apply the aqueous silica slurry can include spray coating or dipping the honeycomb carrier in a silica slurry followed by drying the silica at a temperature from about 100° to about 150° C. in a conventional oven. A sufficient amount of silica is coated on the carrier such that the silica coat comprises from about 15% to about 50% by weight, preferably, from about 20% to about 40% by weight of the completed catalyst.

In accordance with this invention, the silica layer is impregnated throughout with the catalytic metals by known methods. Preferably, an aqueous solution containing a water-soluble palladium and water-soluble gold compound are used as the impregnating agents. Separate solutions of palladium and gold compounds also can be used successively, but it is less convenient to proceed in that fashion. Palladium (II) chloride, sodium palladium (II) chloride, palladium (II) nitrate or palladium (II) sulfate are examples of suitable water-soluble palladium compounds, whereas auric (III) chloride or tetrachloroauric (III) acid can be used as the water-soluble gold compounds. Tetrachloroauric (III) acid and sodium palladium (II) chloride are preferred because of their good water solubility. Quantities of these compounds employed are such as to provide about 1.5 to about 8.0 grams of palladium and about 0.5 to about 8.0 grams of gold per liter of finished catalyst. Gold present in the catalyst will be from about 6% to about 200% by weight relative to the amount of palladium. Catalysts containing even higher or lower amounts of the precious metals relative to that recited above can be useful in formation of vinyl acetate by reaction of ethylene, oxygen and acetic acid in a vapor phase as long as the catalyst comprises a honeycomb carrier with a silica coat which supports the palladium and gold metals.

After impregnation of the carrier with water-soluble palladium and gold compounds, the impregnated carrier can be dried prior to fixing the palladium and gold compounds as water-insoluble compounds on the carrier, or fixing of the palladium and gold compounds can be accomplished while the carrier is still wet with impregnating solution. Fixing solution contains an alkaline solution, for example, an aqueous solution of alkali metal hydroxides, alkali metal bicarbonates and/or alkali metal carbonates. It is particularly preferred to use aqueous solutions of sodium hydroxide or potassium hydroxide. By treatment with an alkaline solution, the water-soluble precious metal compounds are converted to water-insoluble compounds believed to be hydroxides and/or oxides, at least where the alkaline solution is a solution of sodium hydroxide or potassium hydroxide. Alkaline fixing solution simply can be poured onto impregnated carriers and the treated carriers allowed to stand until precipitation of the water-insoluble metal compounds is complete. Volume of fixing solution is that equal to the dry absorbtivity of the carrier and the amount of alkaline compound used is in excess on a molar basis that is required to react with all impregnated precious metal compounds.

Catalyst activity, such as for the formation of vinyl acetate, can be maintained and side reactions relative to the formation of carbon dioxide can be reduced if the fixing step is divided into at least two separate stages of treatment with alkaline fixing solution. In each separate fixing treatment, the amount of the alkaline reactive compound is no more than that equal to the molar amount required to react with all of the precious metal compounds which is present on the carrier as a water soluble compound. No excess of reactive compound is used. Preferably, the amount of reactive compound used in each fixing stage is less than the molar amount required to react with all of the water soluble precious metal compounds. Each fixing stage is conducted by further impregnating the dried impregnated carrier with alkaline fixing solution in an amount equal to about the dry absorbtivity of the carrier. The amount of the alkaline compound contained in solution preferably is such that the ratio of alkali metal to anion from the water soluble precious metal compound is from about 0.7 to about 1:1 molar in the first stage and from about 0.2 to about 0.9:1 molar in the second stage. Preferably, the total amount of alkali metal to anion ranges from about 1.2 to about 1.6:1 molar for the entire fixing step. Subsequent to treatment in the first fixing stage, the treated carriers are allowed to stand for a sufficient period of time to allow precipitation of the water-insoluble precious metal compounds. The period of time can vary but typically ranges from about 2 hours to about 8 hours before the carrier again is treated with the second portion of alkaline fixing solution. Subsequent to treatment in the second fixing stage, the treated supports are allowed to stand again for at least about an additional 2 hours, preferably, at least about 4 hours and can stand to complete precipitation for up to about 16 hours.

Treatment in the second fixing stage can be equivalent to that of the first stage wherein the treated and partially fixed carrier is impregnated with fixing solution at the desired alkaline concentration and in a total volume solution again equivalent to the dry absorbtivity of the carrier. Alternatively, the carrier can be impregnated in the second fixing stage by a process designated rotation immersion disclosed in U.S. Pat. No. 5,332,710, issued Jul. 26, 1994 to Nicolau et al. and assigned to Hoechst Celanese Corporation, the entire disclosure of which is hereby incorporated herein in its entirety by reference. In rotation immersion, the once-fixed catalysts are immersed in alkaline fixing solution and tumbled or rotated therein during the initial stages of precipitation of water-insoluble precious metal compounds. Rotation or tumbling of a carrier in an alkaline fixing solution preferably proceeds for at least about 0.5 hour upon initial treatment and, most preferably, for at least about 1 hour. Rotation immersion treatment can last as long as up to about 4 hours before the treated carriers are allowed to stand in the fixing solution to insure that complete precipitation of the water-insoluble precious metal compounds take place.

Any type of rotation or tumbling equipment can be used as the exact apparatus utilized is not critical. Rotation preferably is sufficient such that all surfaces of the impregnated carriers are evenly contacted with alkaline fixing solution. Rotation preferably is not that harsh such that actual abrasion of the water-insoluble precious metal compounds takes place and that the water-insoluble compounds are abraded off the carrier surface. However, it is believed that some small extent of abrasion of the water-insoluble precious metal compounds works to more evenly distribute the water-insoluble precious metal compounds on the carrier surface. Rotation is about 1 to 10 rpm and even can be higher depending upon the exact carrier utilized and the amount of precious metal to be deposited on the carrier. The rpm is variable and also can depend upon apparatus utilized for rotation, the size and shape of the support, the type of carrier, metal loadings, etc., but preferably falls within the guidelines expressed above that while a small amount of abrasion can be beneficial, it is not such that the water-insoluble compounds are abraded off the carrier surface.

Subsequent to fixing and precipitation, carriers are washed with distilled water to remove anions, such as chlorides, which are still contained on the carrier and freed from the initial impregnating solution. Washing is continued until all anions are removed from the carrier. To ensure substantially complete removal of anions, such as chloride ion, from the catalyst, the wash effluent is tested with silver nitrate after each washing. Washing is continued until the silver nitrate test is negative, i.e., no conversion to silver chloride. The catalyst then is dried at temperatures not to exceed about 150° C. under an inert atmosphere such as a continuous nitrogen flow.

The fixed and washed material then is treated with a reducing agent in order to convert precious metal compounds which are present into metallic form. Reduction can be carried out in a liquid phase, for example, with aqueous hydrazine hydrate, or in a gas phase, for example, with hydrogen or hydrocarbons, for example, ethylene. If reduction is carried out with a solution of hydrazine hydrate, the reaction preferably is carried out at normal temperature. If reduction is carried out in the gas phase, it is advantageous to carry out the reaction at an elevated temperature, for example, at 100°–200° C. when reducing with ethylene. Reducing agent is employed in excess to be certain that all the precious metal compounds are converted into metallic form.

Depending on the use for which the catalyst is intended, the catalyst also can be provided with customary additives. For example, additions of alkali metal salts such as acetates are advantageous when the catalyst is used for preparation of unsaturated esters from olefins, oxygen and organic acids. In such cases, catalysts can be impregnated with an aqueous solution of potassium acetate, sodium acetate, lithium acetate, rubidium acetate or cesium acetate and then dried. Preferably, potassium acetate is the alkali metal salt employed.

Catalysts according to the present invention can be used with particular advantage in preparation of vinyl acetate from ethylene, oxygen and acetic acid in the gas phase. For this purpose, catalysts according to the present invention which are of a metal or ceramic honeycomb carrier coated with silica material and which contain palladium, gold and additives of alkali metal acetates are particularly suitable. In preparation of vinyl acetate, such catalysts also are distinguished by high activity and selectivity and by long life, particularly under commercial operating conditions.

When vinyl acetate is prepared using catalysts of the present invention, a stream of gas which contains ethylene, oxygen or air and acetic acid is passed over the catalyst. The composition of the stream of gas can be varied within wide limits, taking into account explosive limits. For example, the molar ratio of ethylene to oxygen can be about 80:20 to about 98:2 and the molar ratio of acetic acid to ethylene can be about 100:1 to about 1:100 and the content of gaseous alkali metal acetate can be about 2–200 ppm, relative to the acetic acid employed. The stream of gas also can contain other inert gases, such as nitrogen, carbon dioxide and/or saturated hydrocarbons. Reaction temperatures which can be used are elevated temperatures, preferably those in the range of about 150°–220° C. Pressure employed can be a pressure of from about 1 up to about 20 atmospheres gauge.

The following examples are intended to further illustrate the present invention and are not intended to limit the scope of the invention.

EXAMPLES 1 AND 2

Catalysts of Examples 1 and 2 were prepared in accordance with the method of the present invention. Cordierite honeycomb carriers were provided by Corning Inc. and coated with silica by Prototeck Corp. of Needhamm, Mass. Enough silica was coated on each carrier such that the silica comprised about 20% by weight of the entire weight of the completed catalysts. Cordierite 9475, the cordierite honeycomb carrier of Example 1, had a cell density of 400 cells/in$^2$ and weighed about 62.9 gms, and cordierite EX-20, the cordierite honeycomb carrier of Example 2, had a cell density of 200 cells/in$^2$ and weighed about 75.6 gms. Each honeycomb carrier was a cylinder about 45 mm in diameter and about 70 mm long. The absorbtivity of the silica coat on the carrier of Example I was 19.2% while the absorbtivity of the silica coat on the carrier Example 2 was 19.6%.

In both Examples, each silica coated honeycomb carrier was impregnated with an aqueous solution containing sodium palladium chloride and tetrachloroauric acid. A sufficient amount of sodium palladium chloride and tetrachlorauric acid were impregnated on each carrier such that each carrier in the final catalyst was intended to have about 6.6 gm/l of palladium and about 3.0 gm/l of gold. The impregnated carriers were then treated with an aqueous solution of sodium hydroxide having a concentration of about 8 gms/liter. The volume of the sodium hydroxide solution was equal to the dry support absorbtivity in the fixing stage. Each base treated carrier was allowed to stand for about 24 hours. After fixing, each base treated carrier was washed thoroughly with distilled water to remove chloride ions to accepted levels. Washing was continued until the wash effluent would no longer react with silver nitrate. Water flow rate for washing was about 200 cc/min for approximately 5 hours. Each catalyst was dried under a continuous nitrogen flow at a temperature of no more than about 150° C. Each dried catalyst was reduced with ethylene at a temperature of about 150° C. Reducing gas contained about 5% ethylene in nitrogen and was passed over the catalysts for about 5 hours at atmospheric pressure. Each reduced catalyst was impregnated with an aqueous solution containing about 10 grams of potassium acetate at a solution volume equal to the carrier absorbtivity. Each catalyst was dried at a temperature no greater than about 150° C.

Vinyl acetate was prepared using the catalysts prepared in Examples 1 and 2 according to the following procedure. Each honeycomb catalyst was placed into separate baskets suitable in size to hold a single honeycomb catalyst. The baskets with the catalysts were placed in a Berty reactor. A thermocouple was placed on both the top and bottom of each catalyst during vinyl acetate synthesis to measure temperature. Each catalyst was heated by an electric heating mantle placed around the basket holding the catalyst. The catalyst of Example 1 was maintained at about 192° C. and the catalyst of Example 2 was maintained at about 195° C. A gas mixture formed of about 50 normal liters (measured at N.T.P.) of ethylene, 10 normal liters of oxygen, 49 normal liters of nitrogen and about 50 grams of acetic acid was caused to travel under a pressure of about 12 atmospheres over each catalyst. Analysis of product was accomplished by on-line gas chromatographic analysis combined with off-line liquid product analysis by condensing the product stream at 10° C. to obtain optimum analysis of the end products. The results of the analysis of the products from each catalytic synthesis are set forth in Table 1 below.

The honeycomb catalysts of Examples 1 and 2 had high space time yields for vinyl acetate, respectively, of 434 gm/l/hr and 367 gm/l/hr, and comparable $CO_2$ selectivities.

TABLE 1

| CARRIER TYPE | SIZE | CO$_2$ SELECTIVITY | O$_2$ CONVERSION | STY (gm/1/hr) | REACTION TEMPERATURE |
| --- | --- | --- | --- | --- | --- |
| Honeycomb Example 1 | 400 cells/in$^2$ | 14.1% | 48% | 434 | 192° C. |
| Honeycomb Example 2 | 200 cells/in$^2$ | 18.3% | 48% | 367 | 195° C. |

What is claimed:

1. A catalyst for producing vinyl esters comprising a ceramic honeycomb carrier having cells extending the entire length of the carrier, the carrier being provided with a silica coat within at least the cells, the catalyst further comprising palladium metal and gold metal distributed throughout the silica coat.

2. The catalyst of claim 1, wherein the carrier comprises a metal comprising aluminum, titanium, cobalt or steel.

3. The catalyst of claim 1, wherein the carrier is composed of a ceramic material comprising magnesium aluminosilicate, aluminosilicate, or magnesium aluminosilicate-aluminosilicate combination.

4. The catalyst of claim 3, wherein the magnesium aluminosilicate is cordierite.

5. The catalyst of claim 3, wherein the aluminosilicate is mullite.

6. The catalyst of claim 3, wherein the magnesium aluminosilicate-aluminosilicate is cordierite-mullite.

7. The catalyst of claim 1, further comprising an alkali metal acetate uniformly distributed throughout the silica coat.

8. The catalyst of claim 7, wherein the alkali metal acetate comprises potassium acetate, sodium acetate, lithium acetate, rubidium acetate or cesium acetate.

9. The catalyst of claim 8, wherein the alkali metal acetate is potassium acetate.

10. The catalyst of claim 1, wherein the silica-coated cells of the catalyst carrier have a surface area of from about 50 m$^2$/g to about 500 m$^2$/g.

11. The catalyst of claim 1, wherein the catalyst carrier has a density of from 100 cells/in$^2$ to 400 cells/in$^2$.

12. The catalyst of claim 11, wherein the catalyst carrier has a density of from 200 cells/in$^2$ to 400 cells/in$^2$.

13. The catalyst of claim 1, wherein the silica coat comprises from about 15% to about 50% by weight of the catalyst.

14. The catalyst of claim 1, wherein the silica coat comprises from about 20% to about 40% by weight of the catalyst.

15. The catalyst of claim 1, wherein the cells comprise a tubular, square or a hexagonal shape.

16. The catalyst of claim 1, wherein the amount of palladium metal comprises from about 1.5 gm/l to about 8.0 gm/l of the catalyst.

17. The catalyst of claim 1, wherein the amount of gold metal comprises from about 0.5 gm/l to about 8.0 gm/l of the catalyst.

18. The catalyst of claim 1, wherein the amount of gold metal in the catalyst comprises from about 6% to about 200% by weight relative to the amount of palladium metal.

19. The catalyst of claim 1, wherein the pore volume of the carrier comprises less than about 0.4 cc/g as measured by mercury porosimetry.

20. The catalyst of claim 1, wherein the silica coat has micropores with a pore volume of about 0.3 to about 1.0 cc/g.

* * * * *